United States Patent [19]

Hurst et al.

[11] 4,127,217
[45] Nov. 28, 1978

[54] SENSITIVITY DISC DISPENSER WITH TAMPER MECHANISM

[75] Inventors: Philip F. Hurst, Columbia; Jasper Derry, Lothian, both of Md.

[73] Assignee: Becton, Dickinson & Company, East Rutherford, N.J.

[21] Appl. No.: 804,233

[22] Filed: Jun. 7, 1977

[51] Int. Cl.² ............................................. B65H 3/44
[52] U.S. Cl. ..................................................... 221/94
[58] Field of Search .................... 221/93, 94, 95, 264, 221/234, 235

[56] References Cited

U.S. PATENT DOCUMENTS 4,042,145  8/1977  Ehrlich .................................. 221/94

*Primary Examiner*—Stanley H. Tollberg
*Attorney, Agent, or Firm*—Kane, Dalsimer, Kane, Sullivan & Kurucz

[57] ABSTRACT

A sensitivity disc dispenser including a dispensing structure for housing a plurality of disc-containing cartridges and including structure for simultaneously dispensing a disc from each cartridge through each one of a selected number of discharge ports containing a cartridge in a predetermined pattern. The discs are positioned from these cartridges into alignment with the respective discharge port and a tamping mechanism expels the disc through the respective discharge ports into a receiving dish. Controls are provided on the dispenser for moving each disc into and retaining it in a predetermined position and orientation with respect to a selected discharge port and assuring the directing of each disc in the proper orientation by the tamping mechanism onto a receiving surface.

22 Claims, 5 Drawing Figures

SENSITIVITY DISC DISPENSER WITH TAMPER MECHANISM

BACKGROUND OF THE INVENTION

There are many different types of disc dispensers available for dispensing sensitivity discs in a predetermined pattern onto the surface of a culture medium within a receiving dish. Certain types of structures are designed for dispensing a single disc at a time from a single cartridge and others dispense, for example, 8 to 12 discs in a predetermined pattern. With the multi-disc dispensers there are separate disc containing cartridges for each position on the dispenser.

Certain types are rotational dispensing mechanisms where one portion of the dispenser rotates with respect to another portion in order to dispense the discs. Others rely on a reciprocal vertical plunger type of arrangement which employs linkage to dispense a disc from each of the cartridges in the dispenser. In the majority of dispensers which have been used throughout the years, once the dispensers have moved a disc from a cartridge into alignment with a discharge port the disc is permitted to fall freely onto the culture medium. Whatever control is maintained over the disc in its free fall is determined by the diameter of the opening of the discharge port and the length of the surrounding port through which the disc freely falls. Another factor which determines control over the freely falling disc is the height of the bottom open end of the discharge port from the culture medium within the receiving dish.

Examples of dispensers which utilize the freely falling dispensing mechanism when dispensing a plurality of discs simultaneously in a predetermined pattern are disclosed in U.S. Pat. No. 3,394,846 to Carski et al. and U.S. Pat. No. 3,300,087 to Kuypers. Various different approaches from the free fall method of dispensing have been attempted, one of which is the system employed in the Darpentigny et al. U.S. Pat. No. 3,836,047.

The object of all disc dispensers is to be able to provide a selected number of discs in an accurate predetermined pattern for a particular receiving dish and test to be accomplished. The device should be reliable and versatile. It is important that the discs intended to be dispensed on a particular stroke be all dispensed in an accurate and quick and efficient manner as possible. The dispenser is of the type which is reliable in the sense that repeated use will result in the same accurate and complete dispensing of the desired number and pattern of discs. Naturally, cost is also significant and in this respect simplicity of structure is desirable as well as low cost in materials. It should be kept in mind that a simplified structure increases the reliability particularly when dealing with a low cost mass produced device. Different types of antibiotic tests require a different number and arrangement of discs and virtually all tests depend upon accuracy in placement upon the culture medium.

Commonly assigned pending application Ser. No. 628,077 filed Nov. 3, 1975 now U.S. Pat. No. 4,042,145 and entitled Sensitivity Disc Dispenser With Tamper Mechanism represents a recent development in the state of the art relating to sensitivity disc dispensers and particularly in regard to the objects discussed above. The present invention incorporated the basic structure disclosed in that application and adds additional features which represent improvements in the art.

SUMMARY OF THE INVENTION

With the above background in mind, it is among the primary objectives of the present invention to provide a sensitivity disc dispenser which is designed for accurately dispensing a pattern of discs simultaneously of any number from 1 to 12 in a predetermined pattern upon the culture medium in a receiving dish. The dispenser is designed so that upon one dispensing stroke the discs will first be placed into alignment with a dispensing port and then will be subjected to a tamping force to accurately and positively expel the required discs onto the culture medium at the desired position.

The dispensing stroke and the discs when removed from the respective cartridges are closely controlled so that the discs are accurately dispensed and properly oriented at all times with respect to the receiving surface. The objective is to provide the discs in a substantially horizontal position so that they will arrive on the culture surface in a horizontal position. The danger of the discs tipping during their travel path must be alleviated so that they do not arrive on the culture medium in any position other than the proper orientation, as a flat horizontal disc. Also, the discs are controlled so that they are guided throughout their dispensing travel path and there is no danger of clogging or hangup of the discs at any point in their travels from the cartridge through the remainder of the dispensing structure.

As in the above referenced pending application, the structure employs a blocking means to restrain tamping mechanisms from passing through the discharge ports when particular cartridge locations on the dispenser are not being employed. In this manner, it is possible to dispense only a specific number of discs without the necessity of the tamping mechanism passing through the discharge port onto the culture medium at locations where no discs are being dispensed. If the tamping mechanism is allowed to touch the culture medium, cross contamination of the mechanism and culture medium will occur.

This mechanical tamping means is used to eliminate the time-consuming manual tamping of discs required in free falling type disc dispensers. It also reduces the amount of time that the receiving dish must remain open and therefore reduces the chances of airborne contamination of the medium. The mechanical tamping means also provides a means of achieving a consistently precise disc location on the medium and eliminates manual repositioning of discs which are not located in the proper location if they have rolled away from the proper location or do not free fall properly.

The structure is designed so that insertion of a cartridge automatically activates the particular associated tamping mechanism so that only tamping mechanisms in alignment with discharge ports for inserted cartridges are in position to accomplish the tamping action.

It is another objective of the present invention to provide latch means so that the tamping action does not occur until the discs are appropriately dispensed into the discharge ports and are held therein at which time the latch means is released as part of the same dispensing stroke to permit the tamping mechanisms to drive the discs onto the culture surface.

A further object of the invention is to provide a lock mechanism to lock the desired number of cartridges in the appropriate cartridge receiving openings prior to dispensing and tamping operations. Furthermore, in order to provide dimensional clearance with a free operation of the lock mechanism, appropriate protrusions are added to the dispensing structure. The protrusions provide point contacts, and provide for a spacing through which the lock plate can reciprocate between the locked and unlocked positions. In this manner, with only point contact the locking mechanism is permitted free movement in a reciprocal manner while still being held securely enough to lock the cartridges firmly in place.

In addition to providing the spacing operation for the lock mechanism and for the point contacts to facilitate free movement of the lock mechanism, the protrusions provide a control for accurately adjusting the height of the overall dispensing structure which controls the maximum travel of the cam rod, the location of the tamping plate, the location of the tamper plungers in regard to the discs and the location of the dispensing plate. Thus, orientation of a number of moving parts of the dispenser is facilitated by the height control provided by the protrusions on the dispenser.

A still further objective is to ensure that the structure is of low cost design in manufacture and is easy and efficient to use as well as being dependable for multiple use over an extended period of time.

Further objectives of the invention is to provide a number of different controls on the structure to assure that the discs are properly dispensed to a specific location with respect to the discharge ports in the dispenser, are maintained in position for discharge and are dispensed onto the culture surface at the proper location and are properly oriented throughout the entire travel path of the disc onto the receiving surface. The orientation of the discs is never permitted to get out of control to assure that they strike the culture medium other than at the desired orientation, preferably horizontally. Among the structural features which facilitate control and retention of the discs so that they do not fall freely out of control with possible resultant disorientation or hangup or become stuck within the dispensing structure are the following.

The discharge port configuration is formed to enhance delivery of discs without turning over or being delivered on edge. Specifically a constriction is provided at the top of the discharge port such that a disc cannot freely pass through. Additionally a semi-circular disc backstopper is included, causing the disc to be trapped by the dispensing plate fingers against the backstop over the constricted upper portion of the discharge port. The remainder of the discharge port is linearly tapered outward so that the bottom diameter is wider than the constricted upper end to avoid the danger of hangup before the disc is free of the dispenser.

In order to securely and reproduceably trap the disc between the backstop and the dispensing finger, the flat front surface of the cam slide portion of the plunger mechanism is positioned and shaped to stop the dispenser plate from forward travel at precisely the correct spot to trap the disc over the exit constriction. Furthermore, cam guiding surfaces are provided on the inside of the cam slide, on the lower portion of the cam rod of the plunger assembly and in the base supporter of the dispenser to prevent flexing of the plunger assembly in order to ensure that the dispensing plate always reaches its full travel.

Additionally, to further enhance delivery of discs, the tamping plunger tips are configured to provide maximum surface area in contact with the delivered discs. Individual springs are positioned on each tamping plunger, causing the plunger to accelerate during passage through the upper constricted portion of the discharge port, providing extra force where specifically needed and causing the disc being dispensed to remain in intimate contact with the tamping plunger face, thereby exercising more complete control over disc placement on the culture surface.

Additionally, a cam surface is provided on the inside of the dispensing structure in order to provide an engagement surface for the plunger assembly on the return stroke to insure complete return of the dispensing plate through the cam rod and cam slide. The cam surface interferes with the motion of the cam rod and forces the lower end of the cam rod to shift toward the full return of the dispensing plate. Also, a protrusion is formed on the cam rod which serves the tip to cam rod causing the lower end to move in the same direction.

A still further feature of the present dispenser is on the dispensing plate which includes upward projecting posts on one portion of the upper surface of the plate to engage with the interior surface of the dispensing structure when the plate is in the initial non-dispensing position thereby causing the dispensing plate to remain more level and prevent interference by tamping plungers on other portions of the assembly with ejection of discs from the cartridges.

Furthermore, slots are formed in the dispenser structure to mate with protrusions on the underside of the dispensing plate in order to more precisely locate the dispensing fingers with respect to the disc backstop and to reduce the sliding friction caused by surface to surface engagement between the dispensing plate and the supporting structure of the dispenser.

In summary, a sensitivity disc dispenser is provided which includes a dispensing structure for housing a plurality of disc containing cartridges and having means for simultaneously dispensing a disc from each cartridge through each one of a selected number of discharge ports containing a cartridge in a predetermined pattern. Means are provided for positioning a disc from each cartridge into alignment with the discharge port. Tamping means are provided for expelling the disc through the respective discharge ports onto a receiving surface. Means is provided for permitting dispensing through a selected number of ports less than the total number of ports. Finally, control means is provided for moving each disc into and retaining it in a predetermined position and orientation with respect to a selected discharge port and assuring the directing of each disc in the proper orientation by the tamping means onto a receiving surface.

With the above objectives among others in mind, reference is made to the attached drawings.

DESCRIPTION OF THE PREFERRED EMBODIMENT

Figure 1:
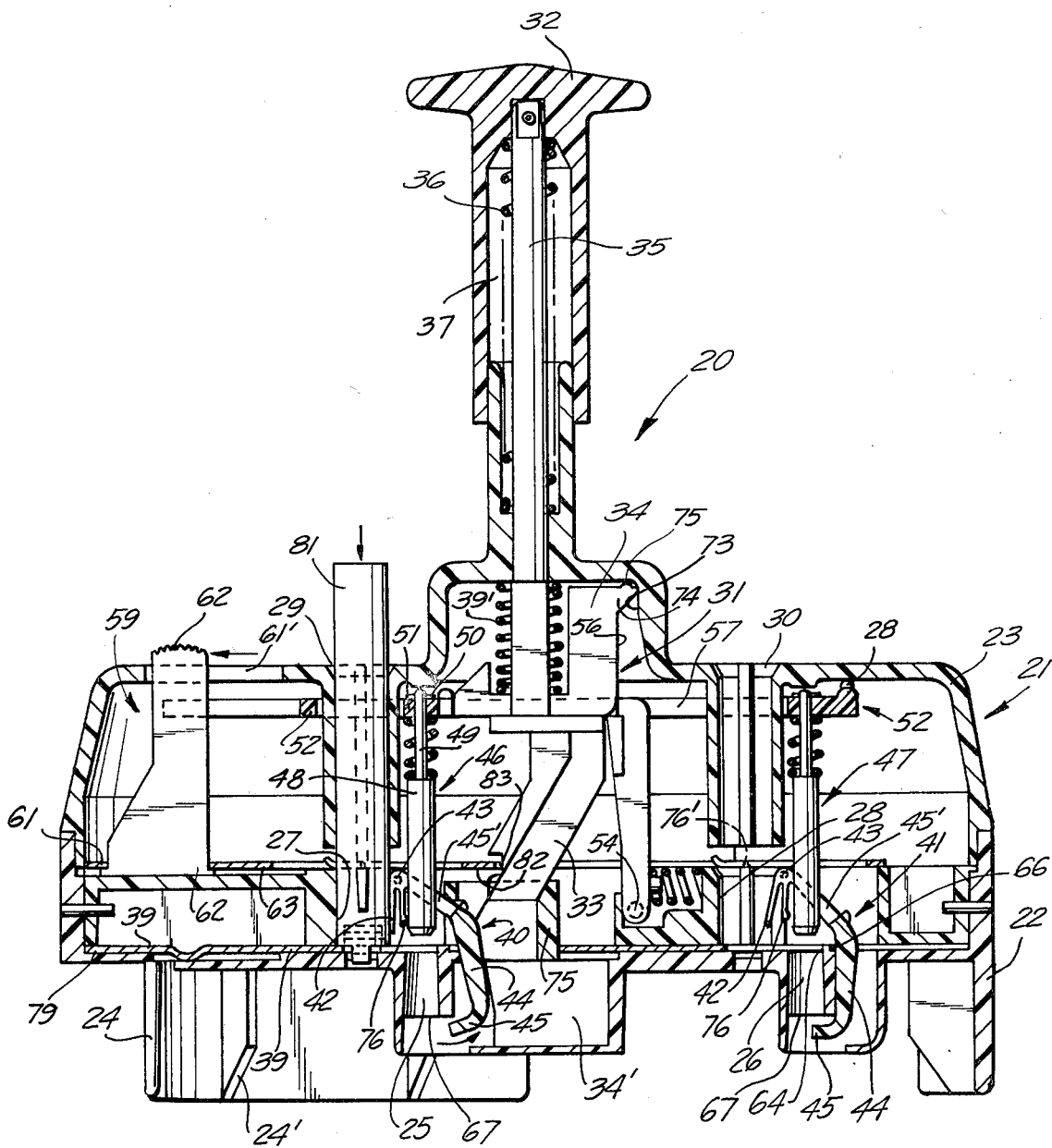
FIG. 1 is a sectional elevation view of the dispenser of the invention with arrows showing the action which occurs upon insertion and locking of a cartridge in position prior to dispensing of a disc.
Figure 2:
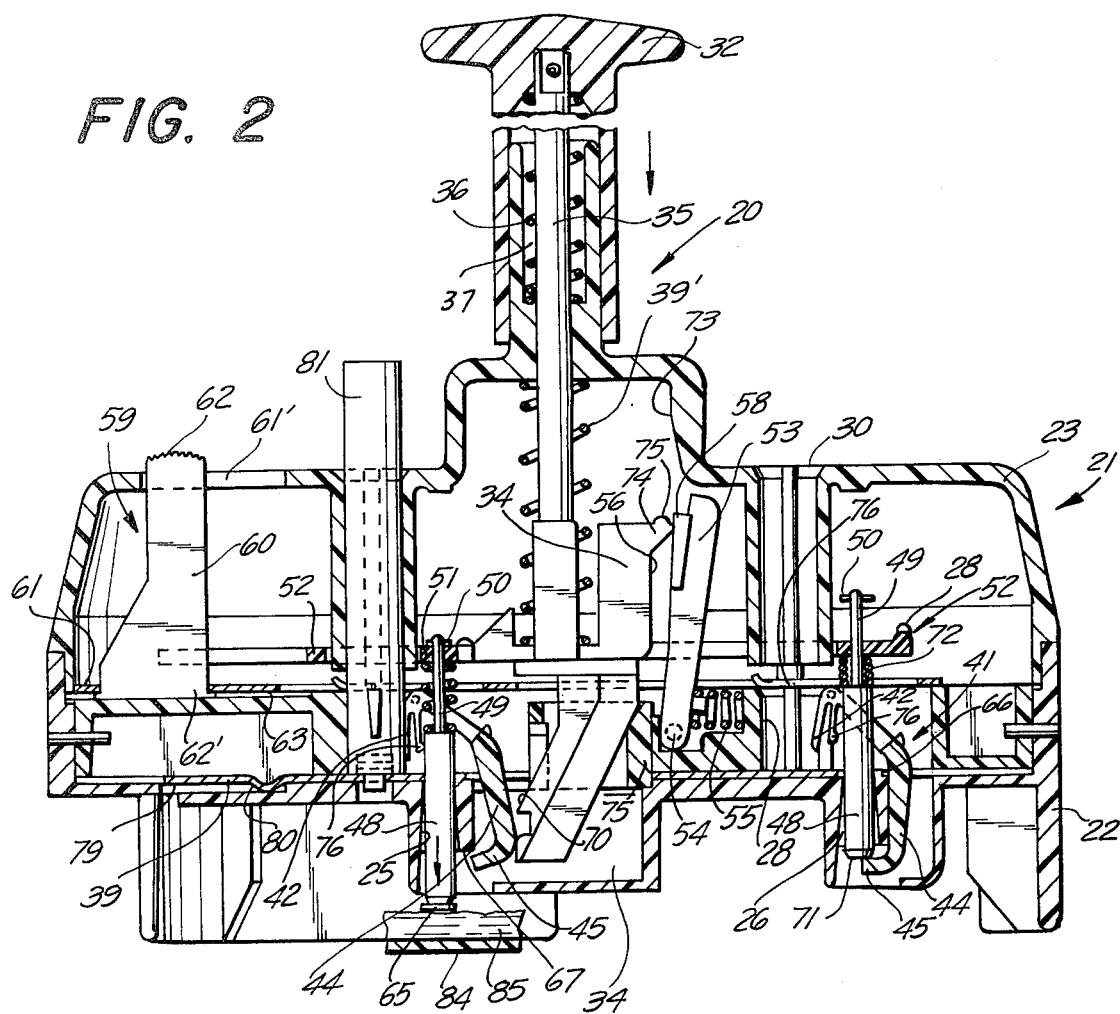
FIG. 2 is a sectional elevation view thereof with a downward dispensing stroke having been completed.
Figure 3:
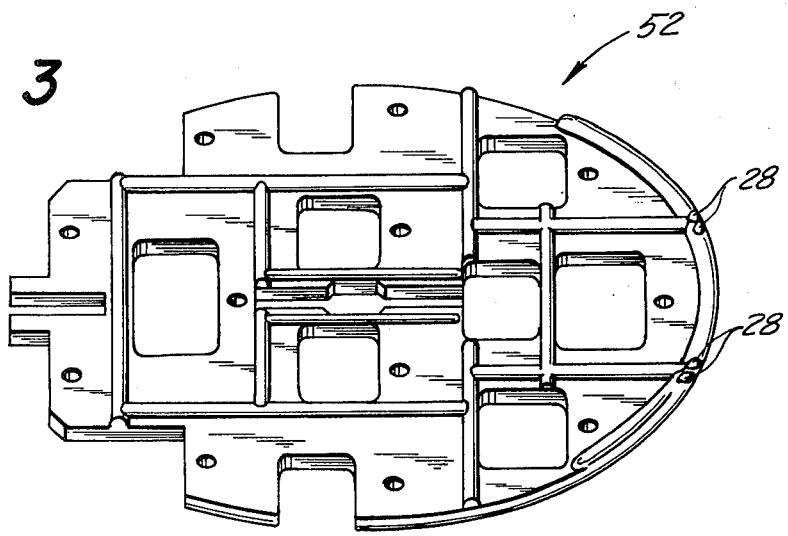
FIG. 3 is a perspective view of the tamping plate portion of the dispenser of the invention.
Figure 4:
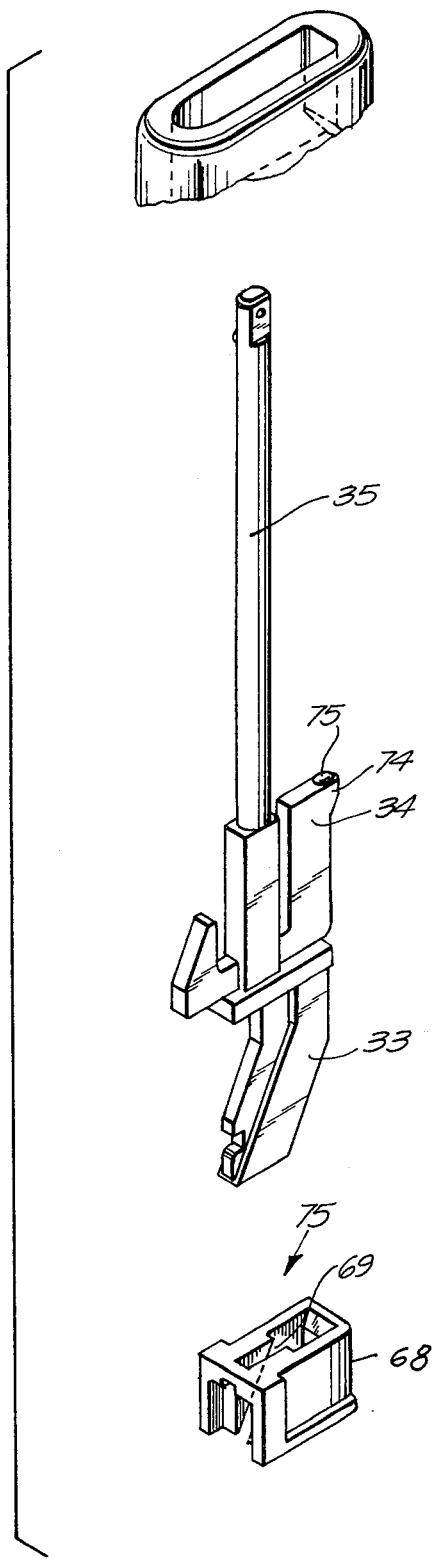
FIG. 4 is an exploded perspective view of the plunger assembly portion of the dispenser of the invention and a fragmentary portion of the structure through which the plunger assembly extends.
Figure 5:
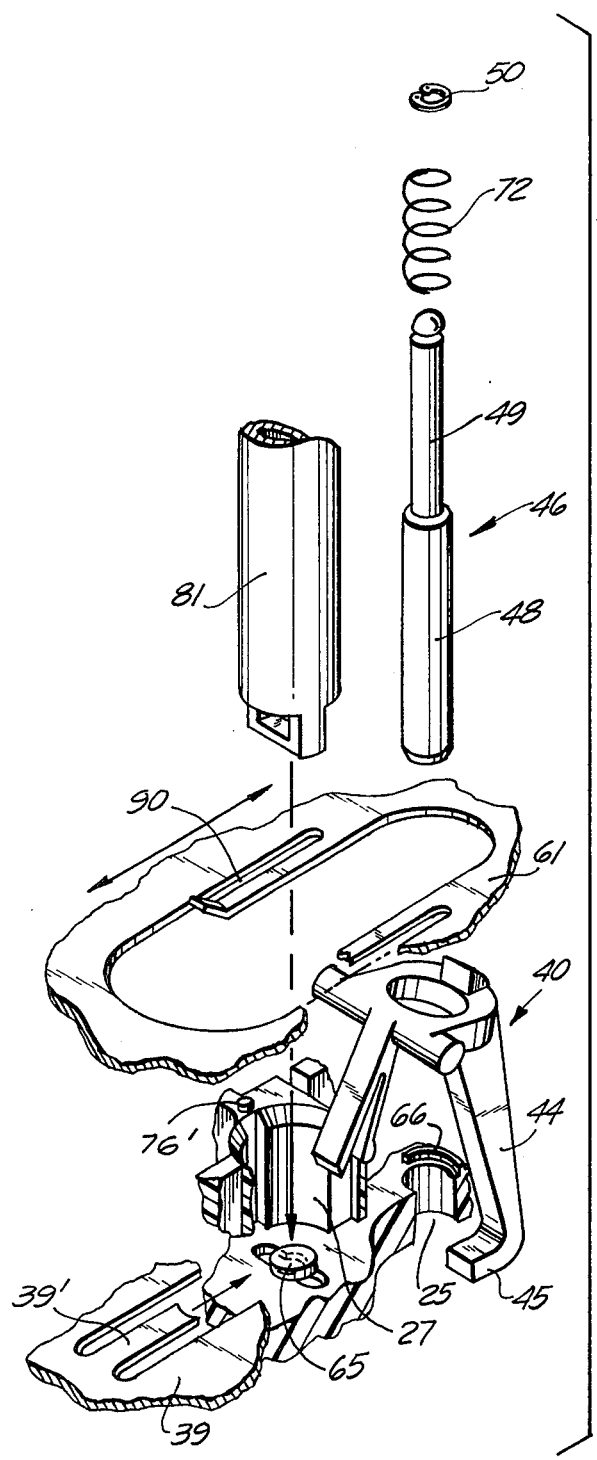
FIG. 5 is an exploded fragmentary partially sectional perspective view of the components surrounding the portion of the dispenser where a disc is dispensed from a cartridge into alignment with a discharge port.

Dispenser 20 includes a dispensing structure or housing 21 including a bottom half 22 and a top half 23. An interrupted skirt 24 extends downwardly from the peripheral bottom edge of bottom half 22 and includes a plurality of inwardly extending vertical ribs 24'. The skirt 24 and the ribs 24' combined to form a guiding surface for directing the dispenser into proper alignment with a culture dish and to form a resting surface for the dispenser over the culture dish during the dispensing operation.

A plurality of spaced discharge ports, such as ports 25 and 26, are located in the hollow interior of dispensing structure 21. There may be any of a number of different arrangement of discharge ports, for example 12, and any number of the ports may be utilized depending upon the particular test and the number of discs to be dispensed in one dispensing sequence.

Adjacent to each discharge port is a cartridge recess or opening such as opening 27 next to discharge port 25 and opening 28 next to discharge port 26. The cartridge openings extend through the dispensing structure and are opened at the top as represented by openings 29 and 30 respectively through which can be extended a cartridge containing discs.

Centrally located in structure 21 is a dispensing plunger assembly 31 which extends out of the upper surface of top half 23 to terminating a dispensing plunger handle or knob 32. The dispensing plunger assembly terminates at the bottom end in an elbow shaped cam rod or arm 33 which is mounted on a cam body 34. A slidable handle rod 35 interconnects with the plunger body and extends through an appropriate opening in the top half 23 of structure 21 and has handle or knob 32 mounted on the upper extremity thereof. A spring 36 is housed in a surrounding recess 37 through which rod 35 extends and is under compression so as to engage with a dispensing structure at one end and an under surface of knob 32 at the other end. Spring 36 tends to bias plunger rod upward with respect to the remainder of dispensing structure 21. A full downward stroke achieved by pressuring knob downward will move plunger rod assembly 31 downward with respect to the housing structure until elbow shaped cam arm is housed in cam receiving chamber 34'. Release of the knob 32 will permit spring 36 to return to its initial slightly compressed condition and shift the entire plunger rod assembly upward to its upward extremity which is determined by engagement between the upper surface of cam body 34 and the under surface of top half 23.

Cam arm 33 extends through a slot in a sliding block or cam slide 75 which is trapped in a dispensing plate 39 and the angular configuration of the elbow shaped cam arm 33 will cause horizontal reciprocation of the dispensing plate upon reciprocal motion of plunger assembly 31 and sliding block 75. This type of action is described in detail in Carski et al. U.S. Pat. No. 3,394,846. Dispensing plate 39 includes appropriate dispensing tabs or fingers for driving a disc from a cartridge within a cartridge recess and bringing it into alignment with the discharge port passageway adjacent thereto.

Each discharge port is associated within a pivotal blocking arm such as arm 40 with respect to discharge port 25 and arm 41 with respect to discharge port 26. Each of these blocking arms includes a shorter activating lever or pin 42 which in the relaxed position extends downwardly and into the adjacent cartridge opening. At the end of the shorter arm 42 each blocking arm is affixed to the inner supporting structure by means of an appropriate pivot pin 43 and then extends in a longer elbow-like lever arm portion 44 which terminates in a blocking tab 45. In the normal relaxed position the shorter pin 42 extends into the adjacent cartridge opening and the longer elbow shaped arm terminating in the locking tab and at the pin is in engagement with the side wall of the discharge passage so that the blocking tab 45 prevents passage of any material or structure from the discharge port. An enlarged opening is in the elbow shaped portion 44 for passage of a tamping mechanism or plunger such as plunger 46 with respect to discharge opening 25 and plunger 47 with respect to discharge opening 26. The openings 45' in the elbow shaped portions are large enough so that the tamping plungers can pass therethrough whether the blocking arms are in the blocking position or shifted to the opened position. The blocking arms such as arms 40 and 41 are spring biased into the closed position by a built-in spring, spring arm 76, or by any other conventional substitute spring means. Alternatively, the spring means can be dispensed with and the arm will remain in the blocking position by normal gravitational forces.

A tamping plunger rod is provided for each discharge opening such as plungers 46 and 47 for discharge openings 25 and 26 respectively and each includes an enlarged body portion 48 at the lower end and a narrower shank portion 49 at the upper end. A locking ring or stop 50 is mounted on the end of the shank 49 distal from the body portion 48. Shank 49 is slidably mounted in opening 51 of a tamping plate 52. The opening 51 for each plunger rod shank 49 is smaller than the diameter of stop 50 and is smaller than the upper surface of body portion 48. Accordingly, movement of plate 52 with respect to the plunger rod is limited by the distance between stop 50 and the upper rim of body 48 of each tamping plunger rod.

Tamping plate 52 is normally retained in the upper position by means of engagement with a latch arm 53 which is pivotally pinned at point 54 to an inner surface on supporting structure 21. A coil spring 55 biases latch arm 53 into the retaining position where it holds plate 52 and accordingly the tamping plunger rod in the upper inactive position. It also holds latch 53 into engagement with dispensing plunger body portion 34 so that it forms a cam follower to follow an appropriate exterior cam surface 56 along the vertical side of body portion 34 as the dispensing plunger rod assembly 31 is directed downward in a dispensing stroke. The upper surface of latch 53 engages with the undersurface of tamping plate 52 to retain it in the upper inactive position prior to activation of the plunger. The arrangement of the components is such that as the dispensing plunger rod assembly 31 is directed downward, dispensing plate 39 is activated to position the appropriate discs into alignment with the respective discharge ports and then further movement of the dispensing rod assembly 31 in the downward direction shifts latch 53 into an appropriate opening 57 in the tamping plate so that the tamping plate can be forced downward onto a receiving surface of the supporting structure by the force of prebiased spring 39' and simultaneously the tamping rods can shift downward until they have expelled appropriate discs from the dispenser or are blocked from further downward movement by engagement with a blocking tab 45 of a blocking arm. Alternatively, in place of helical spring 39', other force mechanisms such as different types of springs can be utilized to direct tamping plate 52 downwardly or, in the alternative, the plate can be permitted to fall freely under the force of gravity onto the receiving surface of the inner supporting structure. Spring 39' is purposely designed to be weaker than spring 36 so that when the plunger is released, spring 36 will overcome this force of spring 39' and return the assembly to the initial position. Cam follower latch 53 contains a tapered follower point 58 which follows cam surface 56 and engages therewith through the force of biasing spring 55. Spring 39' is captured between the undersurface of the top portion 23 of the dispenser and the uppersurface of tamping plate 52. Additionally it surrounds plunger rod 35.

Also provided on the dispensing structure is a lock mechanism 59 which includes a locking bar 60 extending upwardly through opening 61' in the dispensing structure 21 and terminating in a knurled upper surface 62 for finger engagement. Bar 60 is horizontally reciprocal within opening 61' and has its bottom rim 62' slidably channeled in recess 63 within dispensing structure 21. Fitted on locking bar 60 is a locking plate 61 which is horizontally slidable along with the locking bar in a reciprocal direction so as to shift it into locking engagement with cartridges in the cartridge openings 27 and out of engagement with the cartridges when the cartridges are to be introduced or removed from cartridge openings 27. The locking mechanism 59 is quite similar to that shown in U.S. Pat. No. 3,394,486.

Each discharge port has a constricted upper entrance way 64 dimensioned so that the sensitivity disc cannot freely pass through. Additionally, a semi-ciruclar disc backstop 66 is provided at the upper end of each discharge port and diametrically opposed to the point at which the disc is introduced by a dispensing finger of dispensing plate 39. Accordingly, each disc 65 delivered into alignment with a discharge port and is trapped between the ejector plate finger and the adjacent backstop 66 over the constricted upper portion 64 of the discharge port. The remainder of the discharge port is linearly tapered outwardly so that the diameter at the bottom 67 of each port is wider than the diameter of the constricted portion 64.

To facilitate secure and accurate trapping of the disc 65 between the backstop 66 and the finger of the dispensing plate, certain cooperating surfaces are provided on the cam slide, cam rod and dispenser bottom. The flat front surface 68 of the cam slide 75 is positioned to stop the forward travel of the dispensing plate 39 at precisely the correct spot to trap the disc 65 over the aligned discharge port 64. Additionally, cam guiding surfaces 69 are provided in the cam slide 75 to form guideways for the end of the elbow shaped cam rod 33 to pass through. The surfaces 69 are angled to conform to the angle at which the lower end of the cam rod 33 is directed with respect to the vertical direction so that an accurate and positive surface to surface engagement is provided throughout the entire stroke thus facilitating a precise shifting of the dispensing plate. Similarly, the receiving receptacle 34' on the bottom portion 22 of dispenser 21 also has angular guiding surfaces 70 which serve as guideways for the angularly directed lower portion of cam rod 33. These guideways assist in preventing flexing in order to assure that the dispensing plate reach its full travel and the disc is properly trapped against backstop 66.

To further enhance delivery of discs 65, the tamping plunger tip 71 is configured to provide a maximum surface area to contact a disc 65 during the tamping stroke. Thus, the tip has a slight taper at the edges extending into a relatively wide flat tip portion 71 to contact the disc 65.

A helical spring 72 surrounds shank portion 49 of each plunger rod and is captured between the undersurface of tamping plate 52 and the rear surface of the wider portion 48 of the tamping plunger. Each spring 72 causes the plunger to accelerate during passage through the upper constricted portion 64 of the discharge port to provide extra force where needed and to cause the disc 65 to remain in intimate contact with the tamping plunger face 71. In this manner, more complete control is exercised over the disc placement on the culture surface in a receiving dish.

A tapered protrusion in the form of a cam surface 73 is formed on the inner surface of the upper portion 23 of dispenser 21 in position for engagement with body portion 34 of the plunger assembly. This cam surface 73 provides positive drive to the return stroke of the dispensing plate 39 through interengagement between the dispensing plate and the cam rod and cam slide on the plunger assembly. This is accomplished by the interference between protruding surface 73 and the adjacent lateral projection 74 on the cam body 34. As the cam body moves upward to the full return position the protrusion 73 exerts a force on projections 74 which tend to shift the plunger assembly and the interconnected ejector plate so that the ejector plate shifts toward the full return position. Additionally, a projection 75 is positioned on the upper surface of lateral projection 74 to engage with the undersurface of the upper portion 23 of dispenser 21 to cause the plunger assembly, particularly the cam rod portion 33 to tip causing the lower end to move in the same direction, that is full return of the dispensing plate 39 to the initial start position.

In order to provide a dimensional clearance for the free reciprocal sliding operation of the lock plate 61, protrusions 76' are provided on the upper surface of the bottom portion 22. These protrusions mate with the undersurface of upper portion 23. In the embodiment shown, there are 24 protrusions 76' existing in pairs in position adjacent to the cartridge receiving holes in the dispenser. Slots 90 are provided in the lock plate 61 to receive the protrusions 76' and provide a guideway for the plate in its reciprocal movement. These point contacts between the upper and lower portions cause the two parts to be slightly separated more than the thickness of the lock plate 61. This allows the lock plate to move freely back and forth yet still be held securely enough to lock the cartridges firmly in place. Contact with the plate is maintained through the mating protrusions and yet there is not too great an amount of contact which could cause binding of the lock plate in its horizontal reciprocal movement.

An additional function of the protrusions 76' is to control accurately, the height of the top of the cover. The height of the cover is helpful in controlling the maximum travel distance for the cam rod, the location of the tamping plate, the location of the tamping plungers in relation to the discs, and the location of the dispensing plate. While there is one set of 24 protrusions on the depicted embodiment, it is naturally contemplated that other arrangements in number and location are possible to achieve the same results.

Tamping plate 52 is provided with four posts 78 extending upwardly from its upper surface in two pairs in a location where they assist in causing the tamping plate 52 to remain more level and to prevent interference by tamping plungers on the opposite side of the dispenser with ejection of discs from the cartridges. In the depicted embodiment, the posts 78 are located in the same relative angular direction as the protruding surface 58 of the latch arm 53 which supports the tamping plate 52, which is tipped downwardly at the edge opposite to the location of posts 78 during operation. Accordingly, engagement between posts 78 and the undersurface of upper portion 23 will tend to realign the tamping plate to a level horizontal position.

Three slots 79 are formed in the upper side of bottom portion 22 and are positioned to mate with three corresponding protrusions 80 formed on the under side of dispensing plate 39. This relationship provides for more precise location of the dispensing plate fingers with respect to the disc backstops 66 and to reduce the sliding friction between the dispensing plate and engaging surfaces on the supporting structure thus providing improvements in controlling the dispensing action.

In operation, locking mechanism 59 is horizontally withdrawn to free the openings such as openings 27 and 28 to receive cartridges therein. The dispensing plunger assembly 31 is in the inactive upper position under the bias of spring 36 and accordingly the elbow shaped cam arm 33 in the upper position as well. The dispensing plate 39 has been shifted by arm 33 fully to the left thereby eliminating any interference with any portion of cartridge openings. The full shifting is assisted by tipping of the cam arm 33 due to protrusions 73 engaging with lateral projections 74 and projections 75 engaging with upper portion 23. Tamping plate 52 and attached tamping plungers are in the upper position slightly above the latching surface 58 of the latch arm 53, held by the spring 36. The latch arm 53 is held in the latched position and against the body 34 of dispensing plunger assembly 31 by means of compression spring 55. In this position it should be noted that the discharge ports such as ports 25 and 26 are open at the upper end and are blocked at the lower end by blocking tabs 45.

The desired number of cartridges are inserted into the appropriate cartridge openings. The number of cartridges is a matter of choice. For explanation purposes, a cartridge 81 is positioned in opening 27 and opening 28 is left empty. Cartridge 81 is inserted in cartridge opening 27 until it is fully seated at the bottom end. The cartridge is locked in position by shifting cartridge locking bar 62 to the left thereby engaging the body of cartridge 81 by locking plate 61 and retaining it in position. This shifting of plate 61 also unlocks the plunger rod assembly 31 by shifting section 82 of the locking plate 61 away from notch 83 in the rod assembly 31.

Upon insertion of cartridge 81, shorter arm 42 of blocking arm 40 is pivoted down away from opening 27 simultaneously pivoting the longer elbow shaped arm portion 44 up and away from the discharge port 25 adjacent to cartridge opening 27. This action removes blocking tab 45 from the opening at the bottom end of discharge port 25. It should be kept in mind that since no cartridge has been inserted in opening 28, the bottom of discharge port 26 is still blocked by blocking tab 45. The bottom surface of dispensing structure 21 is then positioned over an appropriate receiving dish 84 with a culture medium 85 contained therein. The receiving dish has a bottom wall and a surrounding upperwardly extending peripheral skirt, the upper edge of which receives the undersurface of dispensing structure 21. The skirt is in position for engagement with inward projections 24' on skirt portions 24 at the bottom of the dispenser so that a seating arrangement is provided and the dispenser openings are aligned in proper relationship with the culture surface 85.

Thereafter, the dispensing stroke is initiated by depression of the plunger assembly 31. Partial depression of plunger assembly 31 displaces cam arm 33 in cam slide 75 which then displaces dispensing plate 39 horizontally to displace a disc 65 from the bottom of cartridge 81 so that it is trapped between the dispensing finger 39' on plate 39 and backstop 66 in alignment with constriction 26 of dispensing port 25. Thus, close control is maintained over the disc 65 as it is engaged and shifted into alignment and positioned against backstop 66. No free fall is permitted and the disc is maintained in proper orientation with respect to the culture surface, that is it is not permitted to tip or flip over. Tamping plate 52 and accordingly tamping plungers 46 and 47 are not yet released being retained in position by engagement with latch arm 53 and the tamping action has not occured. Continued downward depression of knob 32 and accordingly dispensing plunger assembly 31 will initiate the tamping action. As discussed above, the movement of the dispensing plate is closely controlled by the appropriate guideways as the plunger assembly is depressed so that a full dispensing stroke is achieved with the disc properly engaged and held against the back stop.

When the knob has been depressed sufficiently, body portion 34 of dispensing plunger 31 will have been shifted downwardly far enough to have its cam surface displace latch arm 53 until it is aligned with opening 57 in tamping plate 52. This permits the tamping plate to be directed downward by spring 39' until it bottoms against a receiving surface on the interior of supporting structure 21. In turn, this permits the tamping plungers 46 and 47 to be driven downward by springs 72.

In the case of plunger 46 with the blocking arm 40 having been shifted from the blocking position, the plunger will travel downward through opening 45 in the blocking arm and through discharge port 25. In this travel path, the tip 71 will engage a disc and drive it through constriction opening 64 in the discharge port and through the remainder of the outwardly tapering port 25 until it drives the disc onto the culture surface 85 in proper position and properly oriented. The intimate contact between the plunger 46 and the disc 65 during the travel donward, maintains the disc in proper orientation in alignment with its terminal location on the culture surface. Thus no disorientation or tipping or flipping of the disc can occur and close control is maintained for the full dispensing action.

The travel length of the tamping plunger will be sufficient to tamp a disc in position at the precise disc spacing location on the culture surface which eliminates the time required to manually reposition discs which may be too close together. The downward movement of plunger 46 will be restrained by the disc contact with the surface of the medium. If the device is activated over nothing or an empty plate, the plunger will be restrained by reengagement of stop 50 at the upper end of shank portion 49 and the upper surface of tamping plate 52 now in the lower position.

In contrast, with respect to tamping plunger 47, it is stopped from full downward movement by engagement between its bottom edge and blocking tab 45 of blocking arm 41. In this manner, the tamping mechanism associated with a cartridge opening not in use is restrained from engaging with and affecting the surface of the culture medium 85. Furthermore, there is no contamination of the unused plunger due to contact with the culture surface 85 or surrounding exposed surfaces.

By permitting the tamping plungers to drive appropriately positioned discs into exact position on the culture surface, the danger of failure of the discs from being fully dispensed from the dispenser on the dispensing stroke is eliminated and additionally the disc is controlled and guided by the tamping plunger to the precise location on the culture medium. Accordingly, reliability and preciseness of displacement and test reliability is achieved.

It should be kept in mind that the entire dispensing operation including the tamping operation is achieved upon one downward stroke of the dispensing plunger assembly 31. When knob 32 is released the plunger assembly 31 will be returned upward to the relaxed position under the bias of spring 36 and will return the tamping plate and tamping plungers to the upper initial positions as well as permitting latch 53 to be returned by spring 55 to its latching position. The dispenser is then ready for repeated use. Plate 52 is carried upward by engaging surfaces on the plunger assembly whicn engage with the undersurface of the plate 52. Naturally the elements of the plunger assembly are interconnected to permit their simultaneous return to the initial position. As the plunger rod portion 33 moves upward it moves the dispensing plate 39 through interconnection with cam slide 75 back to the initial position. As discussed above, this positioning is emphasized by the tipping of the cam assembly due to protrusions 73 and the projection 74 and integral projection 75 on the plunger assembly body portion. Posts 78 hold the tamping plate 52 level while discs are being shucked from the cartridges by the dispensing plate 39. The tamping plate tends to tip when being held up by the latch. The various protrusions on the inside of the structure facilitate horizontal sliding of the locking plate and the mating protrusions and slots facilitate the proper sliding action of the dispensing plate as discussed above. The dispenser is designed to be manufactured of metal or plastic materials and to employ a minimum number of parts that can be quickly and efficiently assembled and operated.

The dispenser is designed to alleviate the danger of contamination of the structure from contact with culture medium so that it can be used repeatedly and so that the operator is not endangered from coming into contact with contaminating materials. To facilitate this condition, the structure is designed so that only the forward tip portions of tamping plungers ever come into contact with the culture medium. Furthermore, should they touch a contaminating surface, the tips 71 of the plungers are slightly beveled so that as they are withdrawn back into the dispensing structure they will not come in contact with any other portions of the structure. Additionally, only the plungers which drive a disc onto the surface extend out of the dispenser and into close relationship to the culture medium. The remaining plungers are held within the dispenser by retaining tabs on the blocking arms. Consequently, there is no danger of plungers coming into direct contact with the culture surface at locations where no discs are being dispensed. It should also be kept in mind that since the tamping plungers are withdrawn back into the dispenser after the dispensing stroke has been completed, there is little danger of contamination of the operator when transporting or handling the dispenser for further use.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

We claim:

1. A sensitivity disc dispenser comprising; a dispensing structure for having a plurality of disc containing cartridges and having means for simultaneously dispensing a disc from each cartridge through each one of a selected number of discharge ports containing a cartridge in a predetermined pattern, including means for positioning a disc from each cartridge into alignment with the discharge port, tamping means for expelling the disc through the respective discharge ports into a receiving dish, means for permitting dispensing through a selected number of ports less than the total number of ports, and control means for moving each disc into and retaining it in a predetermined position and orientation with respect to a selected discharge port and assuring the directing of each disc in the proper orientation by the tamping means onto a receiving surface.

2. The invention in accordance with claim 1 wherein the tamping means includes a plurality of tamping plungers reciprocally mounted within the dispensing structure with each tamping plunger in alignment with a discharge port, a tamping plate reciprocally mounted in the housing and having means thereon to mount the plurality of tamping plungers, each tamping plunger having a main body portion of larger diameter and a stem portion of smaller diameter extending upwardly therefrom, a stop means on the end of the stem distal from the body portion, apertures in the tamping plate with each tamping plunger having its stem slidably mounted in the aperture with the distance of travel of the tamping plunger being determined by the distance between the stop means on the distal end of the stem and the adjacent end of the body portion, the plate being shiftable between an upper inactive condition in which the tamper plungers are each respectively positioned in an aperture in the tamping plate with the stop means on the stem in engagement with the upper surface of the tamping plate and an active condition while the tamping plate is permitted to fall and shift to its lower position whereupon the tamping plungers will correspondingly be permitted to fall downwardly until the body portion extends through the discharge port unless arrested by engagement between some portion of the tamping plunger and an arresting surface.

3. The invention in accordance with claim 2 wherein the control means includes a spring in engagement with each tamping plunger to cause the plunger to accelerate in its downward fall to provide extra force and facilitating the retention of a disc dispensed in intimate contact with the end of the tamping plunger thereby exercising more complete control over the disc as it is dispensed onto a receiving surface.

4. The invention in accordance with claim 2 wherein the end of the main body portion of the tamping plunger distal from the stem portion has a slightly tapered outer surface terminating in a contact tip of sufficient diameter to provide for maximum surface area contact with a disc being dispensed onto the receiving surface.

5. The invention in accordance with claim 2 wherein leveling means is provided on the tamping plate to facilitate retention of the tamping plate in a substantially level position and to guard against interference of plungers with the dispensing of the disc from the cartridge to the receiving surface.

6. The invention in accordance with claim 5 wherein the leveling means includes an arrangement of posts extending upwardly from the upper surface of the tamping plate for engagement with the surrounding dispensing structure.

7. The invention in accordance with claim 1 wherein the control means includes surfaces for engaging with and holding a dispensed disc in fixed position in alignment with the appropriate discharge port for engagement by the tamper means with the disc being positively held in proper orientation.

8. The invention in accordance with claim 7 wherein the engaging means includes a constricted upper end on each discharge port having an outer diameter sufficient to prevent a disc from freely passing through, the remainder of the discharge port tapering linearly outwardly toward the discharge end, a disc backstop positioned adjacent to each discharge port and aligned so that when a disc is dispensed into alignment with the discharge port the backstop will cooperate with the dispensing means to trap the disc therebetween properly oriented and aligned with the constricted upper portion of the discharge port.

9. The invention in accordance with claim 1 wherein the dispensing structure includes a housing, the means for positioning a disc from each cartridge mounted in a cartridge opening in the dispensing structure into alignment with a discharge port includes a reciprocally movable horizontal dispensing plate with a tab and recess for each discharge port and adjacent cartridge opening, a dispensing plunger assembly on the housing and extending into the housing and terminating in a cam surface in engagement with the dispensing plate so that reciprocal movement of the plunger assembly will cause simultaneous reciprocal movement of the dispensing plate for dispensing discs from each cartridge contained in the structure into alignment with a discharge port.

10. The invention in accordance with claim 9 wherein the plunger assembly includes a cam slide in engagement with the dispensing plate and a cam rod interengaged with the cam slide, a predetermined configuration front surface on the cam slide, cam guiding surfaces on the inside of the cam slot and in the supporting structure to cooperate with surfaces on the cam rod to facilitate an accurate travel of the dispensing plate to dispense discs to the correct location in alignment and at the proper orientation with respect to the respective discharge ports.

11. The invention in accordance with claim 9 wherein the plunger assembly includes a cam rod interconnected with a cam slide in engagement with the dispensing plate, the cam rod and the surrounding dispensing structure having appropriately placed camming surfaces to interfere with the motions of the cam rod returning to the initial position before dispensing action begins, the camming surface interfering with the motion of the cam rod and forcing the lower end of the cam rod to shift toward the full return position and accordingly shift the dispensing plate to the full return position.

12. The invention in accordance with claim 11 wherein the cam surface on the dispensing structure includes a projecting portion extending into the path of return of the cam rod to alter the direction of return thereof, and the surface on the cam rod including a projection extending from one portion thereof to engage with the adjacent projecting portion of the dispensing structure when the cam rod is in the full return position to tip the cam rod causing the lower end to move in the same direction toward the full return of the dispensing plate to the initial position.

13. The invention in accordance with claim 9 wherein a plurality of slots are formed in the dispensing structure for alignment with mating protrusions formed on the dispensing plate to form guideways for the dispensing plate in its reciprocal movement between the initial position and the full dispensing position, the aligned slots and mating protrusions acting to more precisely locate the dispensing plate with respect to the disc backstop and to reduce sliding friction caused by the interengagement between the dispensing plate and the surrounding structure of the dispenser housing.

14. The invention in accordance with claim 2 wherein a latch mechanism is provided for release of the tamping plate and tamping plungers, the latch mechanism including a pivotally mounted arm within the dispensing structure, a spring means biasing the arm into engagement with surfaces of the tamping plate to hold the tamping plate normally in an upward inactive position, the arm adapted to be pivoted out of engagement with the surfaces of the tamping plate to permit the tamping plate to fall until it engages with surfaces in the housing to arrest its downward movement.

15. The invention in accordance with claim 2 wherein shiftable blocking means is provided in the dispensing structure shiftable between a position at which it blocks the exit aperture of the discharge port and a position at which it opens the discharge port, the blocking means including a pivotally mounted arm having one shorter leg normally extending into an opening for receiving a cartridge and having a longer irregularly elbow-shaped leg terminating in a blocking tab normally extending at least partially across the opening of the discharge port to thereby prevent discs and a tamping plunger from passing therethrough, the blocking means being pivotally mounted so that when a cartridge is inserted into the recess in the dispensing structure adjacent to a discharge port, the shorter leg will be pivoted away from the opening thereby pivoting the longer elbow-shaped leg and blocking tab away from the exit of the adjacent discharge port so as to permit a disc and tamping plunger to pass therethrough, the blocking means being spring biased into the blocking position by spring biasing means.

16. The invention in accordance with claim 1 wherein seating means is on the dispensing structure to facilitate seating of the structure over a receiving dish with the discharge ports in alignment with receiving surface on the interior of the dish.

17. The invention in accordance with claim 9 wherein a biasing means is provided to bias the plunger assembly upward with respect to the dispensed structure to thereby return the plunger assembly, dispensing plate, and tamping mechanism to the initial inactive position when released after the dispensing stroke is complete.

18. The invention in accordance with claim 1 wherein there are twelve spaced cartridge openings in the dispensing structure.

19. The invention in accordance with claim 9 wherein the plunger is interconnected with the tamping means so that downward movement of the plunger assembly first dispenses a disc from each cartridge into alignment with a corresponding discharge port and then continued downward movement of the plunger assembly activates the tamping means to complete expulsion of the discs through the respective discharge ports into a receiving dish, biasing means being provided to bias the plunger assembly upwardly with respect to the dispensing structure to thereby return the plunger assembly, dispensing plate, and tamping mechanism to the initial inactive position when released after the dispensing stroke is complete, and second biasing means to urge the tamping means downward after activation thereof with the plunger assembly biasing means being greater than the second biasing means thereby facilitating return of the plunger assembly, dispensing plate and tamping mechanism to the initial inactive position.

20. The invention in accordance with claim 1 wherein a lock mechanism is positioned in the dispensing structure and extends through said dispensing structure, the lock mechanism adapted to be shiftable between a first position at which it locks each cartridge in position in the dispensing structure and a second position at which it will permit the cartridge to be inserted or removed from the dispensing structure and can simultaneously prevent the operation of the plunger assembly.

21. The invention in accordance with claim 20 wherein spacing means is provided within the dispensing structure to provide a channel for passage of the locking mechanism reciprocally therethrough thus permitting the locking mechanism to move freely between the locked and unlocked position while still held securely enough by the surrounding structure to lock the cartridge firmly in place.

22. The invention in accordance with claim 21 wherein the spacing means includes a plurality of protrusions on the dispensing structure to separate one portion thereof from the other portion, the protrusions forming point contacts for a guideway for a locking plate portion of the locking mechanism whereby the plate is free to slide in contact with the protrusions which act as holding means for the plate as it moves reciprocally between the locked and unlocked positions.

* * * * *